United States Patent
Nix et al.

(10) Patent No.: US 12,377,277 B2
(45) Date of Patent: Aug. 5, 2025

(54) BIOSTIMULATOR HAVING BURROWING NOSE

(71) Applicant: Pacesetter, Inc., Sylmar, CA (US)

(72) Inventors: Kyle J. Nix, Arcadia, CA (US); Keith Victorine, Santa Clarita, CA (US); Kyungmoo Ryu, Palmdale, CA (US)

(73) Assignee: PACESETTER, INC., Sylmar, CA (US)

( * ) Notice: Subject to any disclaimer, the term of this patent is extended or adjusted under 35 U.S.C. 154(b) by 591 days.

(21) Appl. No.: 17/715,899

(22) Filed: Apr. 7, 2022

(65) Prior Publication Data
US 2023/0321450 A1    Oct. 12, 2023

(51) Int. Cl.
*A61N 1/375* (2006.01)
*A61N 1/05* (2006.01)

(52) U.S. Cl.
CPC ....... *A61N 1/3756* (2013.01); *A61N 1/37512* (2017.08); *A61N 1/37518* (2017.08); *A61N 1/3758* (2013.01); *A61N 1/0573* (2013.01)

(58) Field of Classification Search
CPC .............. A61N 1/3756; A61N 1/37512; A61N 1/37518; A61N 1/3758; A61N 1/0573
See application file for complete search history.

(56) References Cited

U.S. PATENT DOCUMENTS

| | | | | |
|---|---|---|---|---|
| 4,550,737 A | * | 11/1985 | Osypka | A61N 1/057 607/127 |
| 2003/0014099 A1 | * | 1/2003 | Froberg | A61N 1/0573 607/122 |
| 2004/0059401 A1 | * | 3/2004 | Ollivier | A61N 1/057 607/112 |
| 2008/0103572 A1 | * | 5/2008 | Gerber | A61N 1/0534 607/116 |
| 2012/0116489 A1 | * | 5/2012 | Khairkhahan | A61N 1/37518 607/127 |

* cited by examiner

*Primary Examiner* — Eugene T Wu
(74) *Attorney, Agent, or Firm* — WOMBLE BOND DICKINSON (US) LLP (57) ABSTRACT

A biostimulator and a biostimulator system for septal pacing, is described. The biostimulator includes a burrowing nose to allow the biostimulator to embed within a target tissue. The embedded biostimulator has a reduced exposed length within a heart chamber, and is less likely to interfere with adjacent heart structures. Embodiments include burrowing ridges on a nose or a housing of the biostimulator to affix the embedded biostimulator to the target tissue. Other embodiments are also described and claimed.

22 Claims, 8 Drawing Sheets

BIOSTIMULATOR HAVING BURROWING NOSE

BACKGROUND

Field

The present disclosure relates to biostimulators and related biostimulator systems. More specifically, the present disclosure relates to leadless biostimulators and related systems useful for septal pacing.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Leadless cardiac pacemakers incorporate electronic circuitry at the pacing site and eliminate leads, thereby avoiding shortcomings associated with conventional cardiac pacing systems. Leadless cardiac pacemakers can be anchored at the pacing site, e.g., in a right ventricle and, for dual-chamber pacing, in a right atrium, by an anchor. A delivery system can be used to deliver the leadless cardiac pacemakers to the target anatomy.

Cardiac pacing of the His-bundle is clinically effective and advantageous by providing a narrow QRS affecting synchronous contraction of the ventricles. His-bundle pacing in or near a membranous septum of a heart, however, has some drawbacks. The procedure is often long in duration and requires significant fluoroscopic exposure. Furthermore, successful His-bundle pacing cannot always be achieved. Pacing thresholds are often high, sensing is challenging, and success rates can be low.

Pacing at the left bundle branch (LBB) is an alternative to His-bundle pacing. Pacing at the LBB involves pacing past the His-bundle toward the right ventricle apex. More particularly, a pacing site for LBB pacing is typically below the His-bundle, on the interventricular septal wall near the tricuspid valve and pulmonary artery outflow track.

SUMMARY

Existing leadless pacemakers may not fit, or may interfere with cardiac tissue, when placed at the pacing site for left bundle branch (LBB) pacing. More particularly, existing leadless pacemakers having bodies that are long and rigid and, when implanted at the interventricular septal wall, could extend into contact with the cardiac tissue of a ventricular free wall, or even with the tricuspid valve, during contraction of the heart. Furthermore, a proximal end of the existing leadless pacemakers may flail within the heart chamber as the heart beats, causing cyclical contact with the adjacent structures. Contact between the existing leadless pacemakers and the heart structures could interfere with heart function. Additionally, existing leadless pacemakers may not be able to reach the LBB when approaching from the right ventricular septal wall because the electrodes are designed to superficially contact the septal wall rather than be driven deep into the septal wall. Thus, there is a need for a leadless biostimulator that can be engaged to the interventricular septal wall to reach and pace the LBB, and which may be implanted with minimal exposed length in the heart chamber to reduce a likelihood of interfering with adjacent structures of the heart.

A biostimulator is described. In an embodiment, the biostimulator includes a housing containing an electronics compartment to hold pacing circuitry. A nose is mounted on the housing. The nose includes a burrowing ridge to engage and screw into a target tissue. The nose can have a central channel, and a pacing electrode can extend axially in alignment with the central channel. For example, the pacing electrode, e.g., a helical electrode or a post electrode, can extend distal to the central channel. Accordingly, the pacing circuitry can generate and deliver pacing impulses through the central channel to the pacing electrode into the target tissue that the pacing electrode and the nose are embedded within. When embedded within the target tissue, less of the biostimulator is exposed within the heart chamber, and the biostimulator is less likely to interfere with heart structures during contraction of the heart.

The nose has an outer surface and the burrowing ridge has an outer profile. The outer surface and the outer profile can have respective tapered or non-tapered sections. For example, the nose outer surface can include a conical section along which the burrowing ridge extends. The nose outer surface may also (or alternatively) include a cylindrical section along which the burrowing ridge extends. Similarly, the outer profile of the burrowing ridge can have respective cylindrical profile section(s) and/or tapered profile section(s). Accordingly, the nose and the burrowing ridge can have geometries that facilitate screwing and/or plowing into the target tissue, and retaining the biostimulator after embedding in the target tissue.

The housing of the biostimulator, like the nose, can have a housing ridge to screw into the target tissue. The housing ridge can extend along an outer housing surface of the housing, proximally from a distal housing end. The housing ridge can facilitate screwing and/or plowing the housing into the target tissue, and retaining the biostimulator after embedding in the target tissue.

A biostimulator system is described. In an embodiment, the biostimulator system includes a biostimulator transport system, and the biostimulator is mounted on the biostimulator transport system. A method of pacing the target tissue, e.g., a target LBB, using the biostimulator system is also described.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Embodiments describe a biostimulator and a biostimulator system for septal pacing. The biostimulator may, however, be used in other applications, such as deep brain stimulation. Thus, reference to the biostimulator as being a cardiac pacemaker for septal pacing is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes a burrowing nose to embed a portion of the biostimulator in the target tissue. For example, the burrowing nose can be at a distal end of the biostimulator, and can be screwed into a septal wall such that the portion of the biostimulator is embedded in the septal wall. Therefore, less of the biostimulator is exposed within the heart chamber external to the septal wall. The exposed portion is less likely to interfere with the surrounding heart structures during contraction of the heart. In an embodiment, the burrowing nose and a helical electrode of the biostimulator provide a system of helices that can reach the left bundle branch (LBB) through the septal wall and affix the biostimulator to the septal wall.

Figure 1:
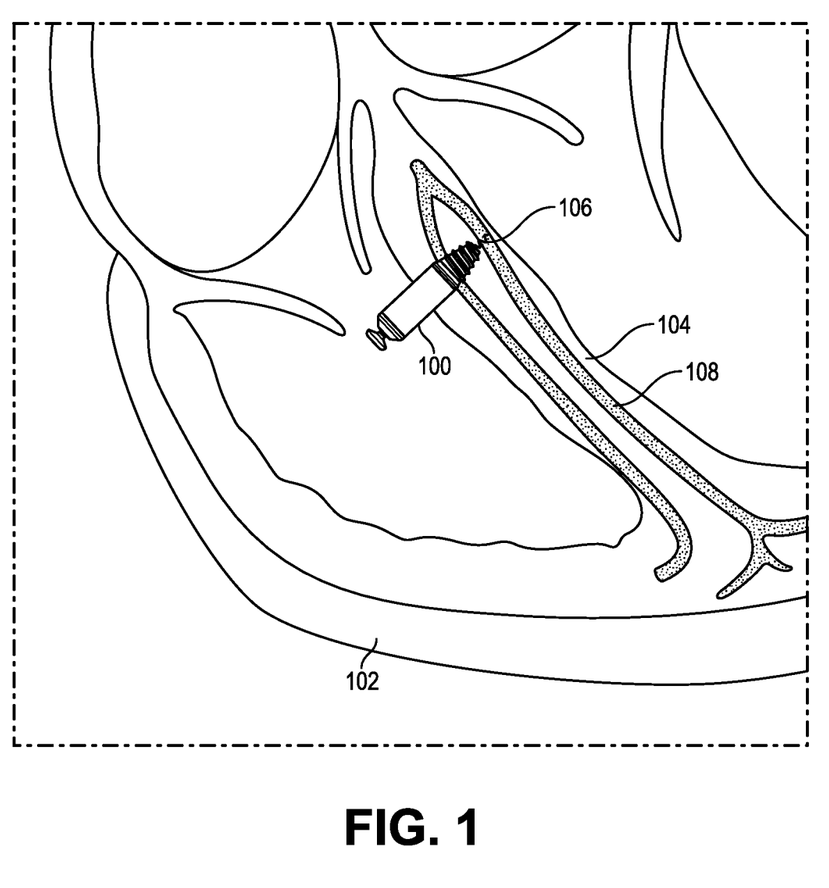
FIG. 1 is a diagrammatic cross section of a patient heart illustrating an example implantation of a biostimulator in a target anatomy, in accordance with an embodiment.

Referring to FIG. 1, a diagrammatic cross section of a patient heart illustrating an example implantation of a biostimulator in a target anatomy is shown in accordance with an embodiment. A leadless biostimulator system, e.g., a cardiac pacing system, includes one or more biostimulators 100. The biostimulators 100 can be implanted in a patient heart 102, and can be leadless (and thus, may be leadless cardiac pacemakers). Each biostimulator 100 can be placed in a cardiac chamber, such as a right atrium and/or right ventricle of the heart 102, or attached to an inside or outside of the cardiac chamber. For example, the biostimulator 100 can be attached to an interventricular septal wall 104 of the heart 102. More particularly, the biostimulator 100 can be delivered to the septum, and one or more elements, such as a pacing electrode 106 can pierce the interventricular septal wall 104 of the septum to engage and anchor the biostimulator 100 to the tissue. Accordingly, the pacing electrode 106 can be located to effectively probe and pace a bundle branch 108 within the interventricular septal wall 104. More particularly, the biostimulator 100 may deliver pacing impulses through the pacing electrode 106 to the bundle branch 108.

Leadless pacemakers or other leadless biostimulators can be delivered to or retrieved from a patient using delivery or retrieval systems. The leadless biostimulator system can include delivery or retrieval systems, which may be catheter-based systems used to carry a leadless biostimulator 100 intravenously to or from a patient anatomy. The delivery or retrieval systems may be referred to collectively as transport systems, or biostimulator transport systems. Examples of transport systems are described below. In some implementations of biostimulator systems, a leadless pacemaker is attached, connected to, or otherwise mounted on a distal end of a catheter of the biostimulator transport system. The leadless pacemaker is thereby advanced intravenously into or out of the heart 102. The transport system can include features to engage the leadless pacemaker to allow fixation of the leadless pacemaker to tissue. For example, in implementations where the leadless pacemaker includes an active engaging mechanism, such as a burrowing nose or a helical fixation element, the transport system can include a docking cap or key at a distal end of the catheter, and the docking cap or key may be configured to engage the leadless pacemaker and apply torque to screw the active engaging mechanism into or out of the tissue. In other implementations, the transport system includes clips designed to match the shape of a feature on the leadless pacemaker and apply torque to screw the active engaging mechanism into or out of the tissue.

Figure 2:
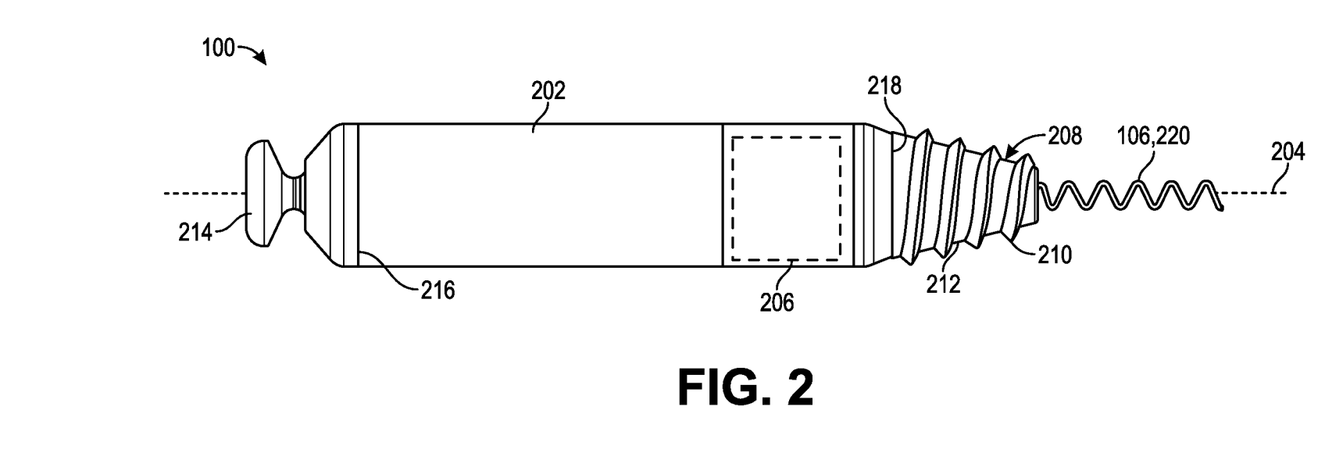
FIG. 2 is a side view of a biostimulator having a burrowing nose, in accordance with an embodiment.

Referring to FIG. 2, a side view of a biostimulator having a burrowing nose is shown in accordance with an embodiment. The biostimulator 100 can be a leadless cardiac pacemaker that can perform cardiac pacing and that has many of the advantages of conventional cardiac pacemakers while extending performance, functionality, and operating characteristics. In a particular embodiment, the biostimulator 100 can use two or more electrodes located on or within a housing 202 of the biostimulator 100 for pacing the cardiac chamber upon receiving a triggering signal from at least one other device within the body. The biostimulator 100 can have two or more electrodes, e.g., a portion of the pacing electrode 106 that acts as an active electrode and/or a portion of the housing 202 that acts as an active electrode. The electrodes can deliver pacing pulses to bundle branches 108 within the septum of the heart 102 to perform deep septal pacing, and optionally, can sense electrical activity from the muscle. The electrodes may also communicate bidirectionally with at least one other device within or outside the body.

The biostimulator 100 includes the housing 202 having a longitudinal axis 204. The housing 202 can contain a primary battery to provide power for pacing, sensing, and communication, which may include, for example, bidirectional communication. The housing 202 can optionally contain an electronics compartment 206 (shown by hidden lines) to hold circuitry adapted for different functionality. For example, the electronics compartment 206 can contain pacing circuitry for sensing cardiac activity from the electrodes, for receiving information from at least one other device via the electrodes, for generating pacing pulses for delivery to tissue via the pacing electrode 106, or other circuitry. The electronics compartment 206 may contain circuits for transmitting information to at least one other device via the electrodes and can optionally contain circuits for monitoring device health. The circuitry of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site, e.g., at the septal wall, by one or more actively engaging mechanism or fixation mechanism. For example, the fixation mechanism can include a screw or helical member that screws into the myocardium. In an embodiment, the biostimulator 100 includes a nose 208 mounted on the housing 202. The nose 208 can include a fixation element to affix and/or embed the biostimulator 100 within the target tissue. More particularly, the nose 208 can include a burrowing ridge 210 to screw into the target tissue. The burrowing ridge 210 may be on a nose outer surface 212 of the nose 208. For example, the burrowing ridge 210 can extend helically along the nose outer surface 212 to form a ridged thread. The ridged thread can engage and screw into the target tissue when the housing 202 is rotated.

In an embodiment, torque can be transmitted to the biostimulator 100 through an attachment feature 214 to rotate the housing 202 and screw the burrowing ridge 210 into the target tissue. The attachment feature 214 can be mounted on a proximal housing end 216 of the housing 202. More particularly, the attachment feature 214 can be mounted on an opposite end of the housing 202 from a distal housing end 218 on which the nose 208 is mounted. The attachment feature 214 can facilitate precise delivery or retrieval of the biostimulator 100. For example, the attachment feature 214 can be formed from a rigid material to allow a delivery or retrieval system to engage the attachment feature 214 and transmit torque through the housing 202.

In an embodiment, the pacing electrode 106 extends along the longitudinal axis 204. For example, the pacing electrode 106 can include a helical electrode 220 extending helically about the longitudinal axis. The helical electrode 220 can include a wire or filament extending helically about the longitudinal axis 204. Over its length, the helical electrode 220 can revolve about longitudinal axis 204. The helical pacing electrode 220, like the burrowing ridge 210 of the nose 208, can screw into the target tissue. When the pacing electrode 106 engages the target tissue, the housing 108 can be advanced and/or rotated to cause the helical electrode 220 to anchor the biostimulator 100. Accordingly, the pacing electrode 106 may both pace the septal wall 104 as well as affix the biostimulator 100 to the septal wall.

As described below, the pacing electrode 106 may alternatively be a post electrode (FIG. 8) having a linear or conical element to pierce into the target tissue. Other electrode configurations are also contemplated. For example, the pacing electrode 106 may be a passive electrode or a tined electrode. Accordingly, the electrode structures described herein are provided by way of example and not limitation.

Figure 3:
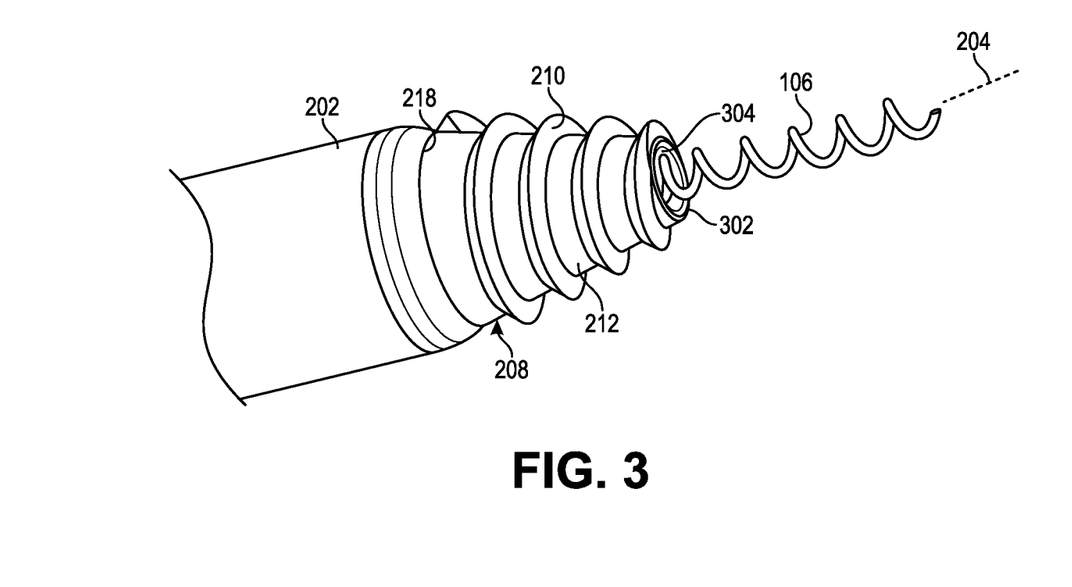
FIG. 3 is a perspective view of a distal portion of a biostimulator having a burrowing nose, in accordance with an embodiment.

Referring to FIG. 3, a perspective view of a distal portion of a biostimulator having a burrowing nose is shown in accordance with an embodiment. The nose outer surface 212 can have a profile conducive to embedding within the target tissue. In an embodiment, the nose outer surface 212 is tapered in a distal direction. More particularly, an outer dimension or diameter at the distal housing end 218 may be greater than an outer dimension or diameter at a distal nose end 302. Accordingly, the nose outer surface 212 may have a tapered conical profile over at least a portion of a nose length such that the nose 208 can plow into and embed within the target tissue when the burrowing ridge 210 is screwed into the target tissue.

The burrowing ridge 210 can protrude radially outward from a base at the nose outer surface 212 to a ridge edge at an outermost radial location. For example, the burrowing ridge 210 may have a triangular cross-section having a wide base and sides that converge to a point at the outermost radial location. Alternatively, the burrowing ridge 210 can include a fin extending radially outward and/or proximally or distally from the base, similar to an auger blade. Accordingly, the burrowing ridge 210 can have a cross-sectional shape that includes the ridge edge to engage and/or protrude into surrounding tissue, and a side surface that slides long the tissue during rotation and resists back out or dislodgment from the tissue when the nose 208 is embedded.

A width of the burrowing ridge 210 may be constant or varied over the length of the nose 208. For example, the width of the ridge base can increase or decrease in the proximal direction. As the ridge base increases, a slope of the sidewalls of the ridge extending from the base to the edge may increase. Accordingly, the burrowing ridge 210 may become less gradual and more resistant to dislodgment when pulled in the longitudinal direction. The burrowing ridge width may therefore be varied to make some sections of the nose 208 easier to engage the tissue, and other sections of the nose 208 more resistant to dislodgment from the tissue.

The nose 208 may include a central channel 304 extending through a body of the nose 208 along the longitudinal axis 204. The central channel 304 provides a passage through which the pacing electrode 106 of the biostimulator 100 may pass or be electrically connected to circuitry contained within the electronics compartment 206. In an embodiment, the pacing electrode 106 extends along the longitudinal axis 204 distal to the central channel 304. For example, a proximal portion of the pacing electrode 106 may be contained within the central channel 304 and a distal portion of the pacing electrode 106 may be exposed distally from the central channel 304. Alternatively, the pacing electrode 106 may be entirely exposed distally from the central channel 304 and connected to an electrode support, e.g., a post, that extends proximally from a proximal end of the pacing electrode 106 through the central channel 304.

Figure 4:
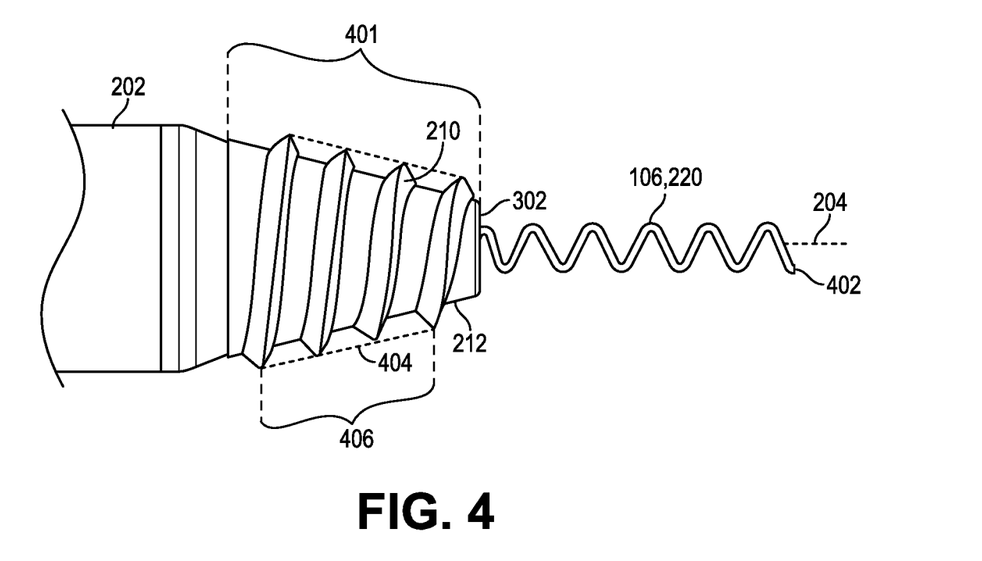
FIG. 4 is a side view of a distal portion of a biostimulator having a burrowing nose, in accordance with an embodiment.

Referring to FIG. 4, a side view of a distal portion of a biostimulator having a burrowing nose is shown in accordance with an embodiment. The exposed pacing electrode 106 can engage the target tissue to reach the target bundle branch 108 distal to a location at which the nose 208 is embedded during operation. In an embodiment, the pacing electrode 106 has a distal electrode tip 402. The distal electrode tip 402 can be a piercing tip that engages and drives through the target tissue toward the target bundle branch 108. The distal electrode tip 402 can be separated from the distal nose end 302. More particularly, the distal electrode tip 402 can be distal to and/or spaced apart from the distal nose end 302 along the longitudinal axis 204. The distance between the distal electrode tip 402 and the distal nose end 302 may be selected such that the distal electrode tip 402 reaches the target bundle branch 108 when the nose 208 is engaged with the target tissue. For example, the distal electrode tip 402 may be separated from the distal nose end 302 by at least 1 mm, e.g., 3 mm, 6 mm, 10 mm, or more, along the longitudinal axis 204.

The helical electrode 220 may be sized to provide efficient and deep engagement of the target tissue. As described above, the distance between the distal electrode tip 402 and the distal nose end 302 permits deep engagement of the target tissue. The pacing electrode 106, e.g., the helical electrode 220, may have a length of 5-15 mm, e.g., 10 mm, to achieve the deep septal pacing. The pitch of the helical electrode 220 may also provide for rapid engagement of the target tissue. More particularly, the pitch may be chosen to allow the helical electrode 220 to screw deeply into the target tissue with each rotation of the biostimulator housing 202. In an embodiment, the helical electrode 220 has a pitch of 1 mm per turn. Accordingly, when the distance between the distal electrode tip 402 and the distal nose end 302 is 5 mm, five turns are required to advance the biostimulator 100 from the stage at which the pacing electrode 106 pierces the septal wall to the stage at which the nose 208 engages the septal wall.

As described above, the nose outer surface 212 may include a conical section 401 tapering distally toward the distal nose end 302. The conical section 401 can extend over all or a part of the nose length. More particularly, as described below, at least a portion of the nose outer surface 212 may be cylindrical (FIG. 6), or another profile shape. The burrowing ridge 210 of the nose 208 can extend along the conical section 401. Accordingly, an inner profile and a base of the burrowing ridge 210, e.g., at the nose outer surface 212, may have a tapered or conical shape.

Figure 6:
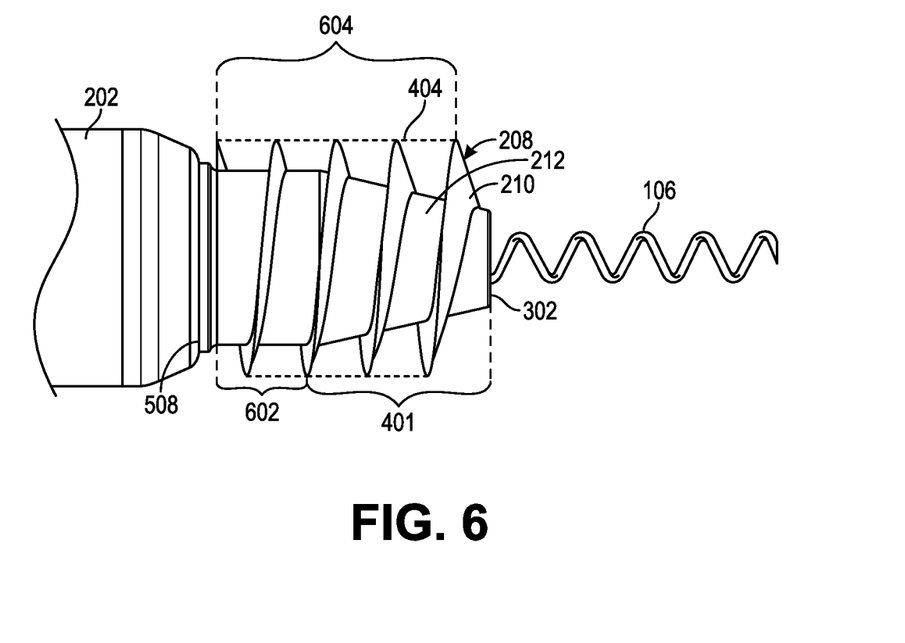
FIG. 6 is a side view of a distal portion of a biostimulator having a burrowing nose, in accordance with an embodiment.

The burrowing ridge 210 can have an outer profile 404 that matches the inner profile. More particularly, when a height of the burrowing ridge 210 from the base to an outer edge of the burrowing ridge 210 is constant over the burrowing ridge length, the outer profile 404 at the edge will match the inner profile at the base. In such case, the outer profile 404 can have a tapered profile section 406 over the conical section 401 of the nose outer surface 212. It will be appreciated, however, that a height of the burrowing ridge 210 may vary over the ridge length, and thus, the outer profile 404 may include a non-tapered profile section 406 (FIG. 6). Accordingly, the outer profile 404 can include one or more of the tapered profile section 406 or the non-tapered profile sections.

Figure 5:
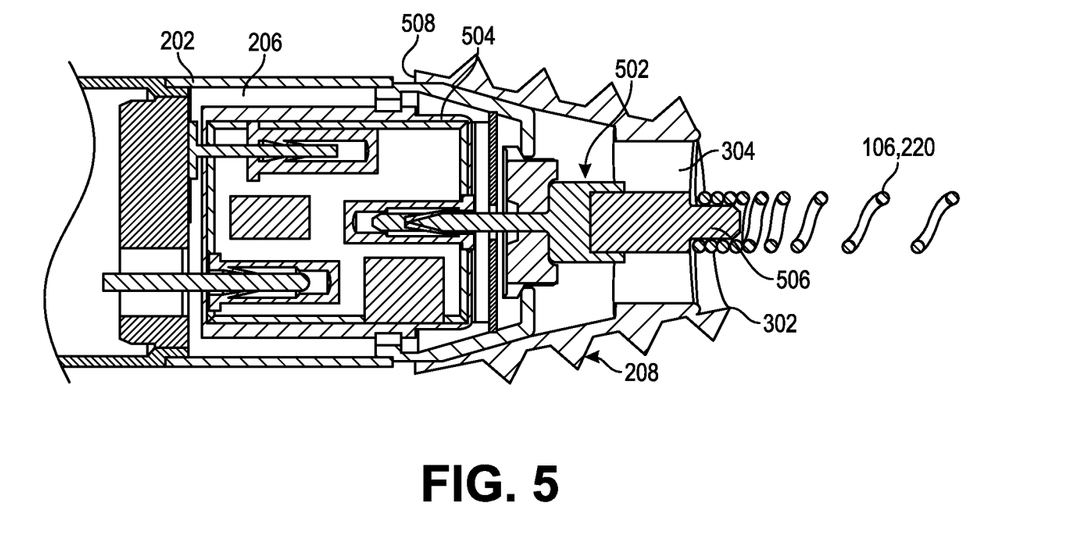
FIG. 5 is a sectional view of a distal portion of a biostimulator having a burrowing nose, in accordance with an embodiment.

Referring to FIG. 5, a sectional view of a distal portion of a biostimulator having a burrowing nose is shown in accordance with an embodiment. The biostimulator 100 can include an electrical feedthrough 502 to transmit pacing impulses from pacing circuitry 504 within electronics compartment 206 to the pacing electrode 106. More particularly, the electrical feedthrough 502 can electrically connect the pacing electrode 106 to the pacing circuitry 504. In an embodiment, the electrical feedthrough 502 is located at least partly within the central channel 304 of the nose 208. For example, a support post 506 on which the pacing electrode 106 is mounted may be located within the central channel 304. A portion of the pacing electrode 106, e.g., a proximal portion mounted on the support post 506, may also be located within the central channel 304. Accordingly, the central channel 304 can contain biostimulator components and provide a passage through which pacing impulses may be delivered to the target tissue.

The central channel 304 of the nose 208 may be used to contain at least a portion of the housing 202 or components within the housing 202. The central channel 304 can extend from a proximal nose end 508 to the distal nose end 302, and the housing 202 or housing components may be contained radially inward from the nose body between those ends. For example, the pacing circuitry 504 may be at least partly within the central channel 304 of the nose 208. By housing at least a portion of the pacing circuitry 504 within the nose 208, either a length of the housing 202 may be shortened or a distance that the nose 208 extends beyond the housing 202 may be reduced. Accordingly, an overall length of the biostimulator 100 and/or a length of the biostimulator 100 exposed within the heart chamber after device implantation may be reduced.

Referring to FIG. 6, a side view of a distal portion of a biostimulator having a burrowing nose is shown in accordance with an embodiment. As described above, the nose outer surface 212 can have tapered and/or non-tapered profile sections. In addition to the conical section 401 of the nose outer surface 212, the nose outer surface 212 may include a cylindrical section 602. The cylindrical section 602 can include a section of the outer surface having a same diameter. The cylindrical section 602 may extend from the proximal nose end 508 to an intermediate transition point. More particularly, the cylindrical section 602 can transition to the conical section 401 at the intermediate transition point. The conical section 401 may extend distally from the transition point to the distal nose end 302. Accordingly, the distal portion of the nose outer surface 212 may be tapered to plow into the target tissue, and a proximal portion of the nose outer surface 212 may be cylindrical to maintain even pressure against the target tissue over a portion of the nose length.

The burrowing ridge 210 can extend along the conical section 401 and/or the cylindrical section 602 of the nose outer surface 212. The ridge includes the outer profile 404 that, like the nose outer surface 212, may include tapered or non-tapered sections. As described with respect to FIG. 4, an entire length of the outer profile 404 may be tapered. Alternatively or additionally, as shown in FIG. 6, the outer profile 404 may include a cylindrical profile section 604. Whereas the tapered profile section 406 of the outer profile 404 includes burrowing ridge outer edges have different major diameters, the cylindrical profile section 604 may include burrowing ridge outer edges having a same major diameter. More particularly, the outer edges of the burrowing ridge 210 within the cylindrical profile section 604 can be a same radial distance from the longitudinal axis 204. Accordingly, the burrowing ridge 210 can grip the target tissue to a same depth along the cylindrical profile section 604.

The burrowing ridge 210 is structured to engage the target tissue and can provide support within the target tissue such that the nose 208 acts as a primary fixation mechanism of the biostimulator 100. The use of tapered or cylindrical sections of the nose outer surface 212 and/or the burrowing ridge 210 can facilitate such fixation. More particularly, the burrowing ridge 210 can be tapered at the same angle as the nose 208, or the burrowing ridge 210 may maintain a constant diameter, as described above. Varying the diameter of the burrowing ridge 210 or maintaining the constant diameter may translate to differing abilities to engage and/or provide support within the target tissue. More particularly, having a maximum surface area of the burrowing ridge 210 engaged with the target tissue may provide more support for fixation, however, the larger burrowing ridge 210 may require more torque to engage the target tissue and could stress the tissue more. Such trade-offs may be considered to provide embodiments of the nose 208 having one or more tapered sections or cylindrical sections on the nose outer surface 212 or the outer profile 404 of the burrowing ridge 210.

Figure 7:
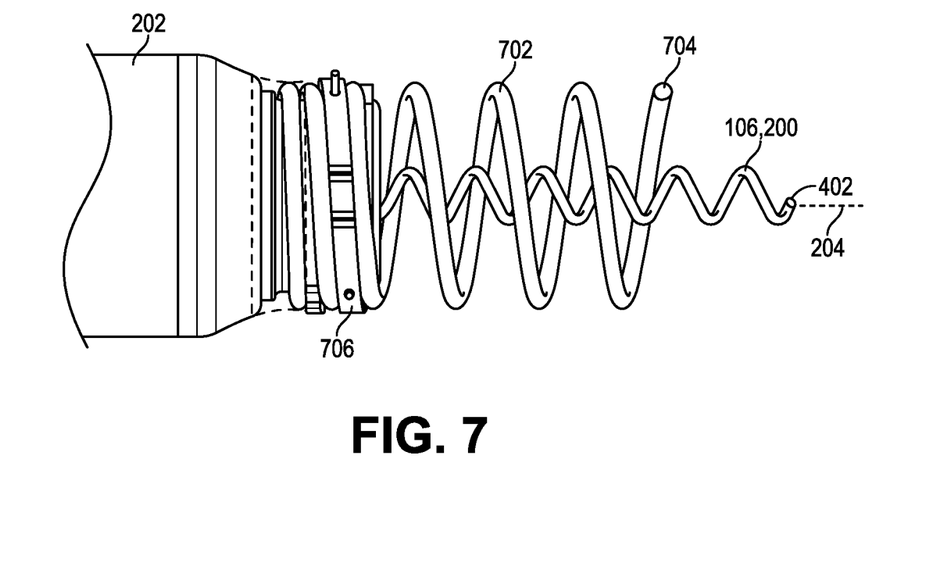
FIG. 7 is a side view of a distal portion of a biostimulator having a fixation helix and a helical electrode, in accordance with an embodiment.

Referring to FIG. 7, a side view of a distal portion of a biostimulator having a fixation helix and a helical electrode is shown in accordance with an embodiment. Instead of or in addition to the nose 208, the biostimulator 100 may include a fixation helix 702 coaxial with the pacing electrode 106. The fixation helix 702 can provide stability within the septal wall when the biostimulator 100 is engaged and implanted therein. The fixation helix 702 can include a wire that extends helically about the longitudinal axis 204 to a piercing tip 704. The fixation helix 702 may be stiffer than the helical electrode 220. More particularly, the fixation helix wire can have a larger diameter and/or a stiffer material than the helical electrode 220. Furthermore, the fixation helix 702 can have a major diameter, e.g., an outer dimension of a helical path of fixation helix 702 wire, that is larger than a major diameter of the helical electrode 220. Accordingly, whereas the helical electrode 220 may be primarily suited toward pacing the target bundle branch 108, the fixation helix 702 may be suited to engaging and supporting the biostimulator 100 within the target tissue.

The fixation helix 702 may allow for deeper fixation within the target tissue as compared to the nose 208 having the burrowing ridge 210. More particularly, the fixation helix 702 may be longer than the nose 208. In an embodiment, a length of the fixation helix 702 is at least half a length of the helical electrode 220. For example, an exposed length of the helical electrode 220 extending to the distal electrode tip 402 beyond a helix mount 706 of the biostimulator 100 may be 10 mm, and a length of the fixation helix 702 extending to the piercing tip 704 beyond the helix mount 706 may be 6 mm. such dimensions are provided by way of example, however, and a ratio between the pacing electrode length and the fixation helix length may vary. For example, the ratio of the fixation helix length to the pacing electrode length may be in a range of 0.25 to 0.75, e.g., 0.6. In the case of an 0.6 ratio, when the biostimulator 100 engages the target tissue, the initial four rotations of the housing 202 can provide pacing engagement between the helical electrode 220 and the target tissue, and the subsequent six turns of the housing 202 can engage the fixation helix 702 to the target tissue to stabilize the biostimulator 100 therein.

Figure 8:
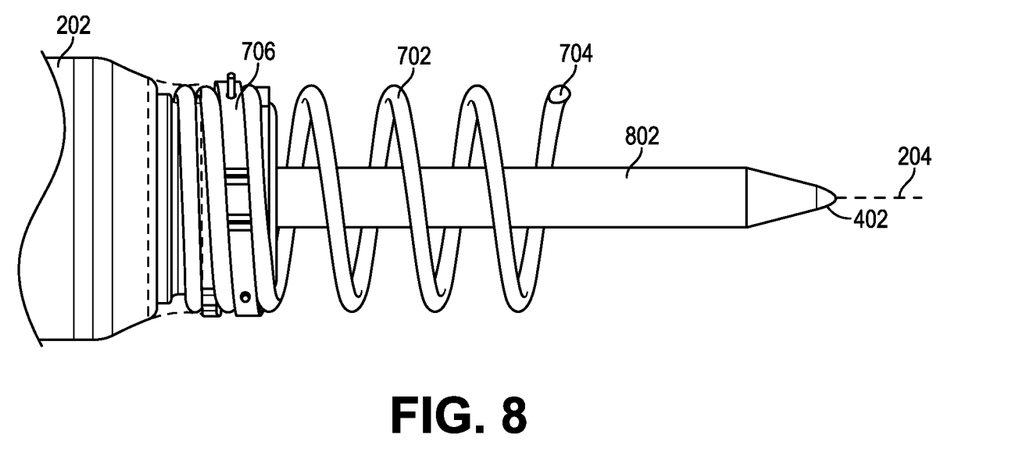
FIG. 8 is a side view of a distal portion of a biostimulator having a fixation helix and a post electrode, in accordance with an embodiment.

Referring to FIG. 8, a side view of a distal portion of a biostimulator having a fixation helix and a post electrode is shown in accordance with an embodiment. The pacing electrode 106 of the biostimulator 100 may include a post electrode 802. The post electrode 802 can include an elongated rod extending distally to the distal electrode tip 402. The distal electrode tip 402 can include a conical piercing tip having a distal point.

The post electrode 802 can extend along the longitudinal axis 204. For example, in an embodiment having the fixation helix 702, the post electrode 802 can extend from the helix mount 706 to the distal electrode tip 402 distal from the piercing tip 704. Similarly, when the post electrode 802 is combined with the nose 208, the post electrode 802 can extend distal from the distal nose end 302 to the distal electrode tip 402.

The post electrode 802 can be pressed axially into the target tissue during device implantation. More particularly, when the biostimulator 100 is delivered to the septal wall, the post electrode 802 can be pressed into the septal wall until the piercing tip 704 contacts the septal wall, and then the housing 202 may be rotated to screw the fixation helix 702 (or the nose 208) into the septal wall and advance the distal electrode tip 402 toward the target bundle branch 108.

Figure 9:
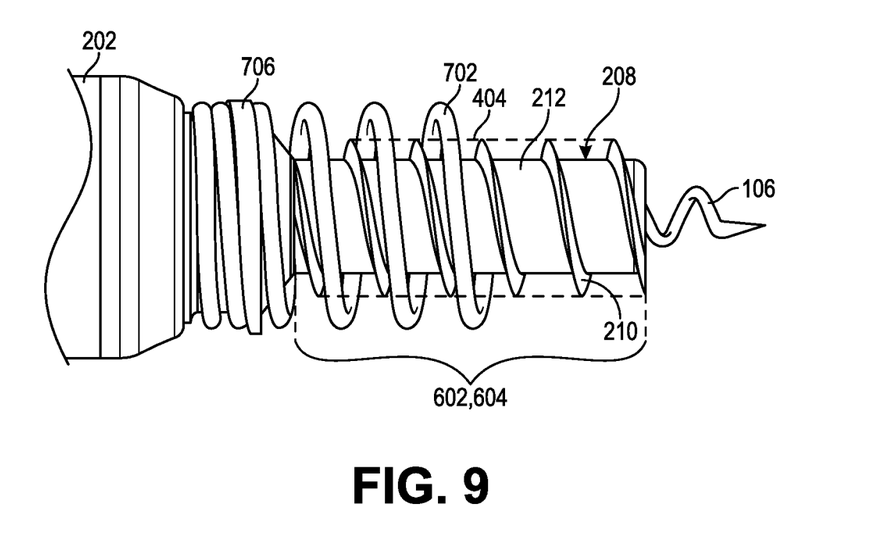
FIG. 9 is a side view of a distal portion of a biostimulator having a fixation helix and a burrowing nose, in accordance with an embodiment.

Referring to FIG. 9, a side view of a distal portion of a biostimulator having a fixation helix and a burrowing nose is shown in accordance with an embodiment. The biostimulator 100 may include the nose 208 and the fixation helix 702. In an embodiment, the fixation helix 702 is mounted on and/or coaxial with the nose 208. For example, the nose 208 may be mounted on the housing 202 of the biostimulator 100, and a proximal portion of the nose 208 may provide the helix mount 706 on which the fixation helix 702 is mounted. Alternatively, the fixation helix 702 may be mounted directly on the housing 202 or helix mount 706 separate from the nose 208, and coaxial with the nose 208. The combination of the fixation helix 702 and the nose 208 may provide additional stability within the target tissue. More particularly, both the burrowing ridge 210 and the fixation helix 702 can engage and grip the target tissue when the biostimulator 100 is implanted therein.

Still referring to FIG. 9, the nose outer surface 212 can have the cylindrical section over its entire length. Similarly, the outer profile 404 of the burrowing ridge 210 can have the cylindrical profile section 604 over its entire length. Outer dimensions of the burrowing ridge 210 and the nose outer surface 212, however, may be less than the major diameter of the fixation helix 702. Accordingly, the nose 208 may be small enough to engage and embed within the target tissue distal from the fixation helix 702, and the fixation helix 702 can stabilize the nose 208 and the pacing electrode 106 by gripping the tissue radially around those components. In any case, the pacing electrode 106 can extend distally from both the nose 208 and the fixation helix 702 to reach the target bundle branch 108.

Figure 10:
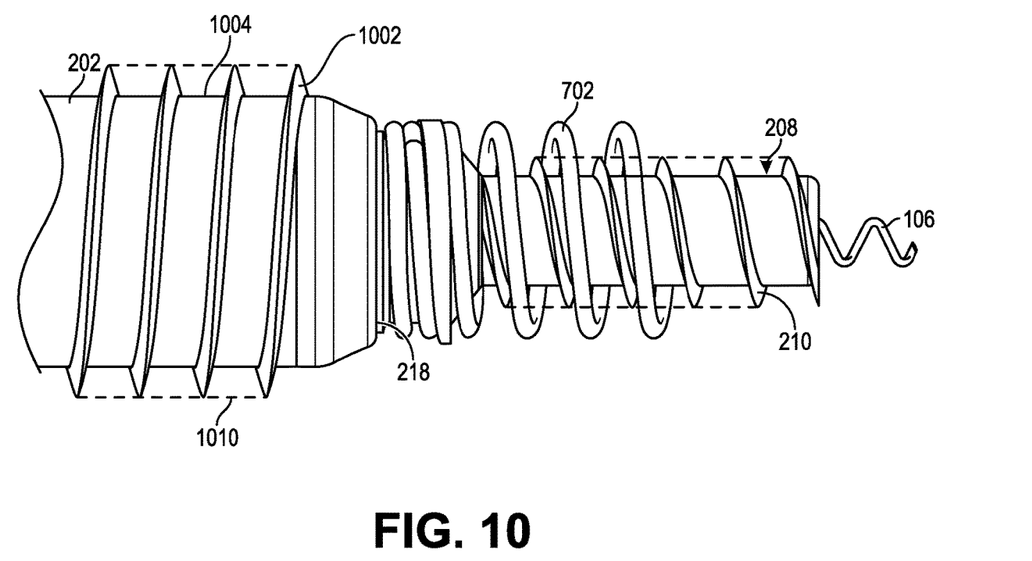
FIG. 10 is a side view of a distal portion of a biostimulator having a fixation helix and a burrowing nose, in accordance with an embodiment.

Referring to FIG. 10, a side view of a distal portion of a biostimulator having a fixation helix and a burrowing nose is shown in accordance with an embodiment. The burrowing ridge 210, or a counterpart to the burrowing ridge 210, may extend onto the housing 202 of the biostimulator 100. For example, in an embodiment, the housing 202 includes a housing ridge 1002 extending along an outer housing surface 1004. The housing ridge 1002 can extend proximally from the distal housing end 218. More particularly, the housing ridge 1002 can extend helically about the outer housing surface 1004 to provide a thread that can engage and advance into the target tissue.

Outer housing surface 1004 can have a cylindrical housing profile and/or a tapered housing profile. For example, as shown in FIG. 10, the outer housing surface 1004 can taper outward in a proximal direction from the distal housing end 218 to the cylindrical portion on which the housing ridge 1002 is located. In an embodiment, the housing ridge 1002 may extend along the tapered portion of the housing 202. An outer profile 1010 of the housing ridge 1002 can have tapered and/or cylindrical sections, similar to the burrowing ridge 210 of the nose 208. Accordingly, it will be appreciated that the structural features of the burrowing ridge 210 may be similarly applied to the housing ridge 1002 to provide a feature that fixes and stabilizes the biostimulator 100 within the target tissue.

Figure 11:
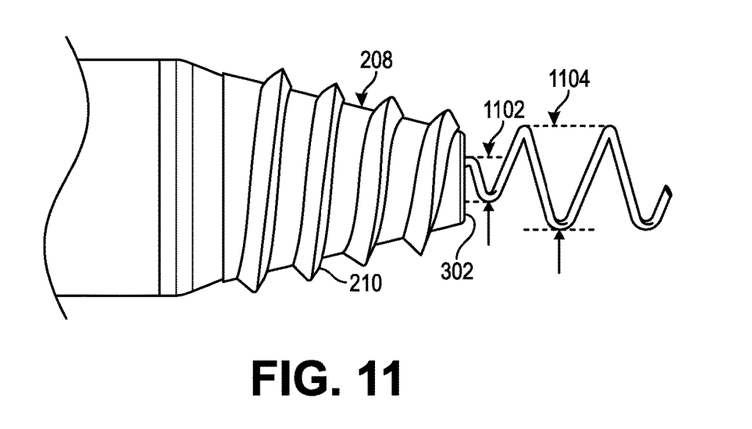
FIG. 11 is a side view of a distal portion of a biostimulator having a variable diameter helical electrode, in accordance with an embodiment.

Referring to FIG. 11, a side view of a distal portion of a biostimulator having a variable diameter helical electrode is shown in accordance with an embodiment. An outer dimension of the pacing electrode 106, like the outer dimension of the burrowing ridge 210 or fixation helix 702, may vary over its length. In an embodiment, a proximal portion of the pacing electrode 106 that extends within the central channel 304 or immediately adjacent to the nose 208 can have a proximal diameter 1102. The pacing electrode 106 may widen distal to the proximal portion. A distal portion of the pacing electrode 106 distal from the proximal portion may have a distal diameter 1104 distal to the nose 208. The distal diameter 1104 may be greater than the proximal diameter 1102. By increasing the diameter of the pacing electrode 106 distal to the nose 208, a major diameter of pacing electrode 106 can approximate the major diameter of the burrowing ridge 210. More particularly, the distal diameter 1104 of the pacing electrode 106 can have a same or similar diameter as the burrowing ridge 210 at the distal nose end 302, and/or the distal nose end 302. Matching the burrowing ridge 210 diameter to the pacing electrode 106 diameter can provide a uniform transition between the pacing electrode 106 used for electrical pacing and the nose 208 used for mechanical stabilization.

Figure 12:
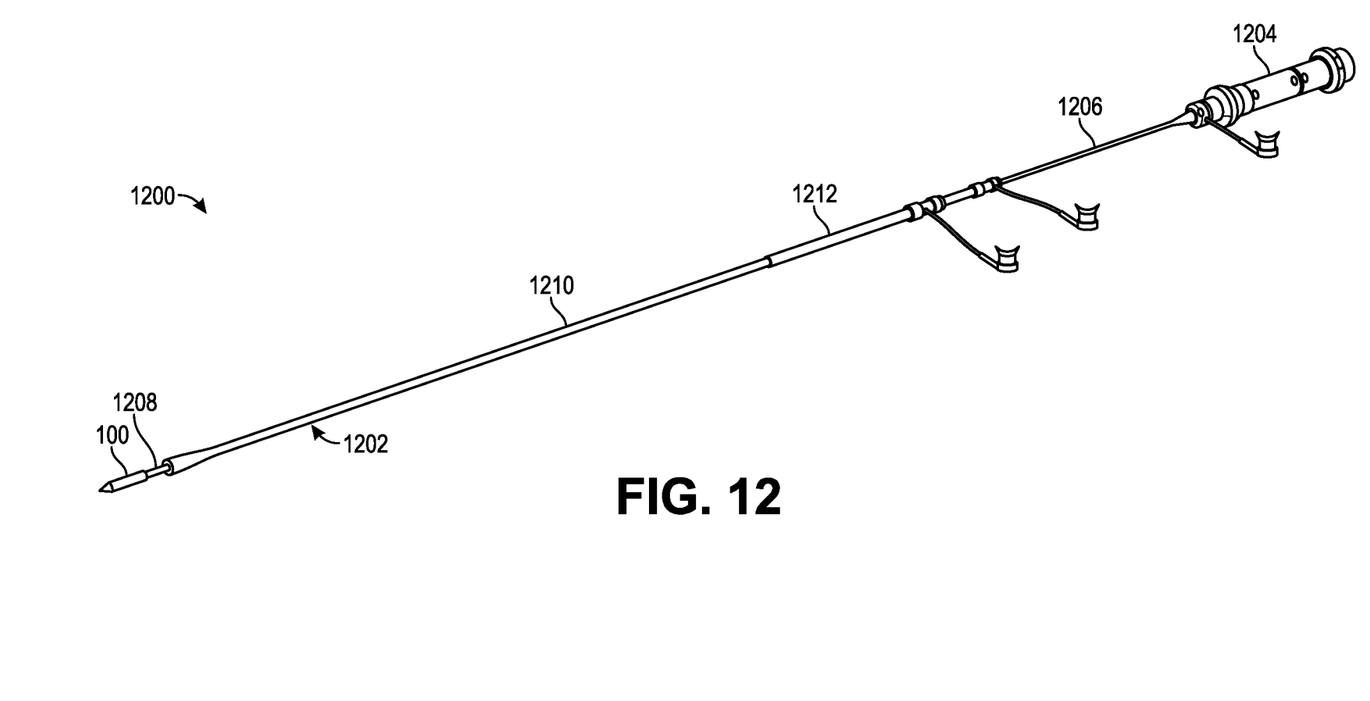
FIG. 12 is a perspective view of a biostimulator system, in accordance with an embodiment.

Referring to FIG. 12, a perspective view of a biostimulator system is shown in accordance with an embodiment. A biostimulator system 1200 can include a biostimulator transport system 1202. The biostimulator transport system 1202 can include a handle 1204 to control movement and operations of the transport system from outside of a patient anatomy. One or more elongated members extend distally from the handle 1204. For example, an outer member 1206 and an inner member 1208 extend distally from the handle 1204. The inner member 1208 can extend through a lumen of the outer member 1206 to a distal end of the transport system. In an embodiment, the biostimulator 100 is mounted on the biostimulator transport system 1202, e.g., at the distal end of one of the elongated members.

The transport system can include a protective sheath 1210 to cover the biostimulator 100 during delivery and implantation. The protective sheath 1210 can extend over, and be longitudinally movable relative to, the elongated members. The transport system may also include an introducer sheath 1212 that can extend over, and be longitudinally movable relative to, the protective sheath 1210. The introducer sheath 1212 can cover a distal end of the protective sheath 1210, the elongated members, and the biostimulator 100 as those components are passed through an access device into the patient anatomy.

Several components of the biostimulator transport system 1202 are described above by way of example. It will be appreciated, however, that the biostimulator transport system 1202 may be configured to include additional or alternate components. More particularly, the biostimulator transport system 1202 may be configured to deliver and/or retrieve the biostimulator 100 to or from the target anatomy.

Figure 13:
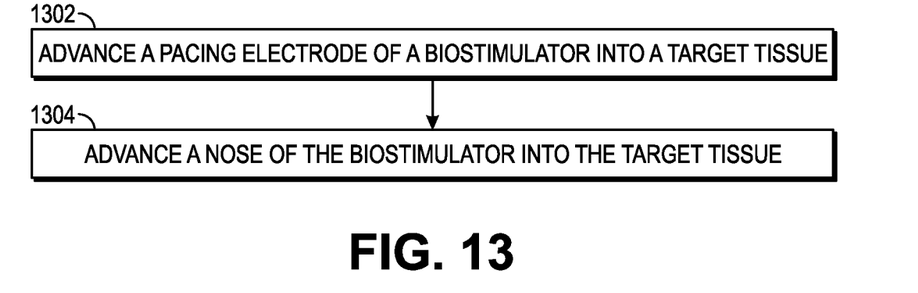
FIG. 13 is a flowchart of a method of implanting a biostimulator for septal pacing, in accordance with an embodiment.

Referring to FIG. 13, a flowchart of a method of implanting a biostimulator for septal pacing is shown in accordance with an embodiment. During the implantation procedure, the biostimulator transport system 1202 can carry the biostimulator 100 into the target heart chamber. When implantation is to be within the right ventricle, the biostimulator transport system 1202 can be tracked through the inferior vena cava into the right atrium and across the tricuspid valve into the right ventricle. The distal end of the transport system can be steered toward a desired location of the septal wall. For example, the target area may be in an upper region of the interventricular septal wall 104.

At operation 1302, the pacing electrode 106 of the biostimulator 100 is advanced into the target tissue. When the biostimulator 100 has the helical electrode 220, the pacing electrode 106 can be advanced by rotating the housing 202. When the biostimulator 100 has the post electrode 802, the pacing electrode 106 can be advanced by pushing the housing 202 forward. In any case, the pacing electrode 106 can penetrate the septal wall 104 and advance toward the target pacing area, e.g., at the target bundle branch 108.

At operation 1304, the nose 208 of the biostimulator 100 is advanced into the target tissue. The nose 208 can be advanced by rotating the housing 202 when the distal nose end 302 is in contact with the septal wall 104. Rotation of the housing 202 can cause the burrowing ridge 210 to engage and screw into the septal wall tissue. When screwed into the septal wall tissue, the biostimulator 100 may have less exposed material within the heart chamber. For example, the nose 208 and a portion of the housing 202 may be embedded under a surface of the septal wall. The embedded portion of the housing 202 may include the housing portion surrounding the pacing circuitry 504, for example. In such case, the pacing circuitry 504 may be considered to be embedded within the septal wall, however, a proximal portion of the housing 202 (proximal to the electronics compartment 206) may be exposed outside of the septal wall within the heart chamber. The embedded biostimulator 100 can have a reduced exposed area, and thus, may be less likely to interfere with adjacent heart structures during heart contraction.

Figure 14:
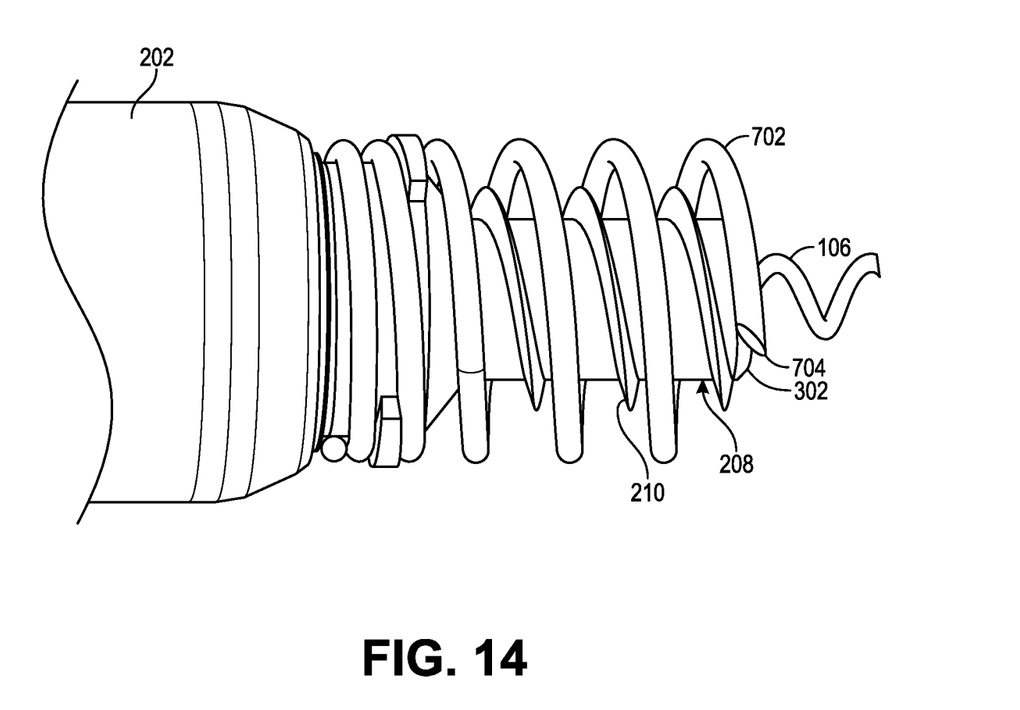
FIG. 14 is a side view of a distal portion of a biostimulator having a fixation helix and a burrowing nose, in accordance with an embodiment.

Referring to FIG. 14, a side view of a distal portion of a biostimulator having a fixation helix and a burrowing nose is shown in accordance with an embodiment. Similar to the embodiments described above, including with respect to FIG. 9, the biostimulator 100 may include the nose 208 and the fixation helix 702. In an embodiment, the piercing tip 704 of the fixation helix 702 is near the distal nose end 302 of the nose 208. As described above, the combination of the fixation helix 702 and the nose 208 may provide additional stability within the target tissue. More particularly, both the burrowing ridge 210 and the fixation helix 702 can engage and grip the target tissue when the biostimulator 100 is implanted therein.

In an embodiment, the fixation helix 702 can extend to the piercing tip 704 at a location adjacent or distal to the distal nose end 302. For example, the piercing tip 704 may be located at a same longitudinal location, or slightly distally (e.g., up to 5 mm) of, the distal nose end. Accordingly, when the biostimulator 100 is delivered to the target tissue, the pacing electrode 106 and the fixation helix 702 can engage the target tissue prior to the burrowing ridge 210. More particularly, the piercing tip 704 contact the target tissue prior to the distal nose end 302, and the housing 202 can be rotated to screw the fixation helix 702 into the target tissue. When the fixation helix 702 is screwed into the target tissue, it can provide forward pressure that draws the nose 208 against the target tissue. More particularly, the fixation helix 702 can bias the nose 208 forward, and thus, forward pressure can be exerted on the nose 208 to engage the distal nose end 302 and the burrowing ridge 210 to the target tissue. Accordingly, additional rotation can cause the burrowing ridge 210 to screw into the target tissue, providing additional stability, in combination with the fixation helix 702, to the biostimulator 100.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator, comprising:
   a housing having a longitudinal axis and containing an electronics compartment;
   a nose mounted on the housing, wherein the nose includes a burrowing ridge on a nose outer surface, and a central channel extending through the nose along the longitudinal axis; and
   a pacing electrode extending along the longitudinal axis, wherein the pacing electrode includes a proximal portion within the central channel and a distal portion distal to the central channel.

2. The biostimulator of claim 1, wherein the nose outer surface includes a conical section, and wherein the burrowing ridge extends along the conical section.

3. The biostimulator of claim 1, wherein the nose outer surface includes a cylindrical section, and wherein the burrowing ridge extends along the cylindrical section.

4. The biostimulator of claim 1, wherein the burrowing ridge has an outer profile, and wherein the outer profile includes one or more of a cylindrical profile section or a tapered profile section.

5. The biostimulator of claim 1, wherein the pacing electrode includes a helical electrode extending about the longitudinal axis.

6. The biostimulator of claim 1, wherein the pacing electrode includes a post electrode extending along the longitudinal axis.

7. The biostimulator of claim 1, wherein the housing includes a housing ridge extending along an outer housing surface.

8. The biostimulator of claim 1, wherein the pacing electrode has a proximal diameter within the central channel and a distal diameter distal to the nose, and wherein the distal diameter is greater than the proximal diameter.

9. The biostimulator of claim 1, wherein the pacing electrode has a distal electrode tip, wherein the nose has a distal nose end, and wherein the distal electrode tip is distal to the distal nose end.

10. The biostimulator of claim 1 further comprising an electrical feedthrough in the central channel, wherein the electrical feedthrough electrically connects the pacing electrode to pacing circuitry within the electronics compartment.

11. The biostimulator of claim 10, wherein the pacing circuitry is at least partly within the central channel of the nose.

12. The biostimulator of claim 1 further comprising a fixation helix coaxial with the nose, wherein the fixation helix includes a piercing tip distal to a distal nose end of the nose.

13. A biostimulator system, comprising:
    a biostimulator transport system; and
    a biostimulator mounted on the biostimulator transport system, the biostimulator including a housing having a longitudinal axis and containing an electronics compartment, a nose mounted on the housing, wherein the nose includes a burrowing ridge on a nose outer surface, and a central channel extending through the nose along the longitudinal axis, and a pacing electrode extending along the longitudinal axis, and wherein the pacing electrode includes a proximal portion within the central channel and a distal portion distal to the central channel.

14. The biostimulator system of claim 13, wherein the nose outer surface includes a conical section, and wherein the burrowing ridge extends along the conical section.

15. The biostimulator system of claim 13, wherein the nose outer surface includes a cylindrical section, and wherein the burrowing ridge extends along the cylindrical section.

16. The biostimulator system of claim 13, wherein the burrowing ridge has an outer profile, and wherein the outer profile includes one or more of a cylindrical profile section or a tapered profile section.

17. The biostimulator system of claim 13, wherein the housing includes a housing ridge extending along an outer housing surface.

18. The biostimulator system of claim 13, wherein the pacing electrode has a proximal diameter within the central channel and a distal diameter distal to the nose, and wherein the distal diameter is greater than the proximal diameter.

19. The biostimulator of claim 13 further comprising a fixation helix coaxial with the nose, wherein the fixation helix includes a piercing tip distal to a distal nose end of the nose.

20. A method, comprising:
    advancing a pacing electrode of a biostimulator into a target tissue, wherein the biostimulator includes a housing having a longitudinal axis and containing an electronics compartment, a nose mounted on the housing, wherein the nose includes a burrowing ridge on a nose outer surface, and a central channel extending through the nose along the longitudinal axis, wherein the pacing electrode extends along the longitudinal axis, and wherein the pacing electrode includes a proximal portion within the central channel and a distal portion distal to the central channel; and
    advancing the nose of the biostimulator into the target tissue.

21. The method of claim 20, wherein advancing the pacing electrode and the nose into the target tissue includes rotating the housing.

22. The method of claim 20, wherein advancing the pacing electrode into the target tissue includes pushing the housing forward, and wherein advancing the nose into the target tissue includes rotating the housing.

* * * * *